US009423374B2

(12) United States Patent
Mackintosh et al.

(10) Patent No.: US 9,423,374 B2
(45) Date of Patent: Aug. 23, 2016

(54) REFERENCE ELECTRODE ERROR TRAP DETERMINED FROM A SPECIFIED SAMPLING TIME AND A PRE-DETERMINED SAMPLING TIME

(71) Applicant: LifeScan Scotland Limited, Inverness (GB)

(72) Inventors: Stephen Mackintosh, Inverness (GB); Antony Smith, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 0 days.

(21) Appl. No.: 14/605,501

(22) Filed: Jan. 26, 2015

(65) Prior Publication Data

US 2016/0216226 A1    Jul. 28, 2016

(51) Int. Cl.
*G01N 27/327* (2006.01)

(52) U.S. Cl.
CPC ...... *G01N 27/3274* (2013.01); *G01N 27/3272* (2013.01); *G01N 27/3273* (2013.01)

(58) Field of Classification Search
CPC .................................... G01N 27/327–27/3274
See application file for complete search history.

(56) References Cited

U.S. PATENT DOCUMENTS

| 4,919,770 | A | | 4/1990 | Preidel et al. |
| 5,352,351 | A | * | 10/1994 | White .................. G01N 27/3273 |
| | | | | 204/403.04 |
| 5,366,609 | A | * | 11/1994 | White .............. G01N 33/48792 |
| | | | | 204/403.04 |
| 7,258,769 | B2 | | 8/2007 | Cui et al. |
| 7,972,861 | B2 | | 7/2011 | Deng et al. |
| 2004/0079652 | A1 | | 4/2004 | Vreeke et al. |
| 2005/0103624 | A1 | * | 5/2005 | Bhullar .................. C12Q 1/001 |
| | | | | 204/403.01 |
| 2008/0083618 | A1 | | 4/2008 | Neel et al. |
| 2009/0194432 | A1 | | 8/2009 | Deng |
| 2009/0223834 | A1 | | 9/2009 | Cai et al. |
| 2009/0236237 | A1 | | 9/2009 | Shinno et al. |
| 2010/0206749 | A1 | | 8/2010 | Choi |
| 2010/0276303 | A1 | | 11/2010 | Fujiwara et al. |
| 2010/0283488 | A1 | | 11/2010 | Nakamura et al. |
| 2015/0001070 | A1 | | 1/2015 | MacKintosh |
| 2015/0068922 | A1 | | 3/2015 | MacKintosh |

FOREIGN PATENT DOCUMENTS

| WO | 2006070200 A1 | 7/2006 |
| WO | 2013098563 A1 | 7/2013 |
| WO | 2013098564 A1 | 7/2013 |
| WO | 2013098565 A1 | 7/2013 |

OTHER PUBLICATIONS

U.S. Appl. No. 61/530,795, filed Sep. 2, 2011.
U.S. Appl. No. 61/530,808, filed Sep. 2, 2011.

(Continued)

*Primary Examiner* — Alexander Noguerola

(57) ABSTRACT

Various embodiments for a method that allow for a more accurate analyte concentration with a biosensor by determining at least one physical characteristic of the sample and determining whether a counter or reference electrode is causing an error by monitoring the working electrodes and flagging an error if the signal outputs of the working electrodes do not meet certain thresholds.

6 Claims, 10 Drawing Sheets

(56) References Cited

OTHER PUBLICATIONS

Wegener J. et al., "Electric Cell—Substrate Impedance Sensing (ECIS) as a Noninvasive Means to Monitor the Kinetics of Cell Spreading to Artificial Surfaces," Experimental Cell Research 259, 158-166 (2000) doi:10.1006/excr.2000.4919.

Kohma, T. et al., "Utilization of AC Impedance Measurements for Electrochemical Glucose Sensing Using Glucose Oxidase to Improve Detection Selectivity," Bull. Chem. Soc. Jpn. vol. 80, No. 1, 158-165 (2007).

U.S. Appl. No. 13/929,404, filed Jun. 27, 2013.

International Search Report and Written Opinion issued in related International Patent Application No. PCT/EP2016/051455, mailed May 23, 2016, 11 pages.

* cited by examiner

Start of Test Sequence

REFERENCE ELECTRODE ERROR TRAP DETERMINED FROM A SPECIFIED SAMPLING TIME AND A PRE-DETERMINED SAMPLING TIME

BACKGROUND

Electrochemical glucose test strips, such as those used in the OneTouch® Ultra® whole blood testing kit, which is available from LifeScan, Inc., are designed to measure the concentration of glucose in a physiological fluid sample from patients with diabetes. The measurement of glucose can be based on the selective oxidation of glucose by the enzyme glucose oxidase (GO). The reactions that can occur in a glucose test strip are summarized below in Equations 1 and 2.

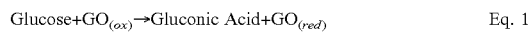

Eq. 1

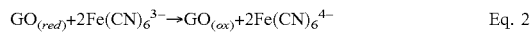

Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test signal applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose signal.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration as compared to referential analyte concentration) is observed at low hematocrit. At high hematocrit, for example, the red blood cells may impede the reaction of enzymes and electrochemical mediators, reduce the rate of chemistry dissolution since there is less plasma volume to solvate the chemical reactants, and slow diffusion of the mediator. These factors can result in a lower than expected glucose reading as less signal is produced during the electrochemical process. Conversely, at low hematocrit, fewer red blood cells may affect the electrochemical reaction than expected, and a higher measured signal can result. In addition, the physiological fluid sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cells and attenuate the effect of low hematocrit on concentration determinations. Other test strips have included lysis agents and systems configured to determine hemoglobin concentration in an attempt to correct hematocrit. Further, biosensors have been configured to measure hematocrit by measuring an electrical response of the fluid sample via alternating current signals or change in optical variations after irradiating the physiological fluid sample with light, or measuring hematocrit based on a function of sample chamber fill time. These sensors have certain disadvantages. A common technique of the strategies involving detection of hematocrit is to use the measured hematocrit value to correct or change the measured analyte concentration, which technique is generally shown and described in the following respective US Patent Application Publication Nos. 2010/0283488; 2010/0206749; 2009/0236237; 2010/0276303; 2010/0206749; 2009/0223834; 2008/0083618; 2004/0079652; 2010/0283488; 2010/0206749; 2009/0194432; or U.S. Pat. Nos. 7,972,861 and 7,258,769, all of which are incorporated by reference herein to this application.

SUMMARY OF THE DISCLOSURE

Applicant has devised analyte measurement system that includes a test strip and an analyte meter. The test strip includes a substrate, plurality of electrodes connected to respective electrode connectors with a reagent disposed proximate the plurality of the electrodes. The meter includes a housing, a test strip port connector configured to connect to the respective electrode connectors of the test strip, and a microprocessor in electrical communication with the test strip port connector to apply electrical signals or measure electrical signals from the plurality of electrodes. The microprocessor is configured to: (a) apply a first signal to the plurality of electrodes so that a physical characteristic of a fluid sample is determined; (b) apply a second signal to a first electrode and a second electrode of the plurality of electrodes; (c) measure a signal output from the electrodes proximate the specified sampling time point from each of the first and second electrodes; (d) measure another signal output from the electrodes proximate a predetermined sampling time point from each of the first and second electrodes; (e) calculate a first differential between a signal output of the first electrode measured at the specified sampling time point and a signal output of the first electrode measured at the predetermined sampling time point; (f) calculate a second differential between a signal output of the second electrode measured at the specified sampling time point and a signal output of the second electrode measured at the predetermined sampling time point; (g) evaluate whether any one of the first differential and second differential is less than a predetermined threshold; and (h) in the event one of the first and second differentials is less than the bias threshold then annunciate an error.

Accordingly, in any of the embodiments described earlier, the following features may also be utilized in various combinations with the previously disclosed embodiments. For example, the plurality of electrodes may include four electrodes with the first and second electrodes to measure the analyte concentration and third and fourth electrodes to measure the physical characteristic; the first, second, third and fourth electrodes are disposed in the same chamber provided on the substrate; the first and second electrodes and third and fourth electrodes are disposed in respective two different chambers provided on the substrate; all of the electrodes are disposed on the same plane defined by the substrate; a reagent is disposed proximate the at least two other electrodes and no reagent is disposed on the at least two electrodes; the final analyte concentration is determined from the second signal within about 10 seconds of a start of the test sequence and the bias threshold may include any value from about 10 nanoamperes to about 1000 nanoamperes; the sampling time point is selected from a look-up table that includes a matrix in which different qualitative categories of the estimated analyte are set forth in the leftmost column of the matrix and different qualitative categories of the measured or estimated physical characteristic are set forth in the topmost row of the matrix and the sampling times are provided in the remaining cells of the matrix In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user.

Figure 1A:
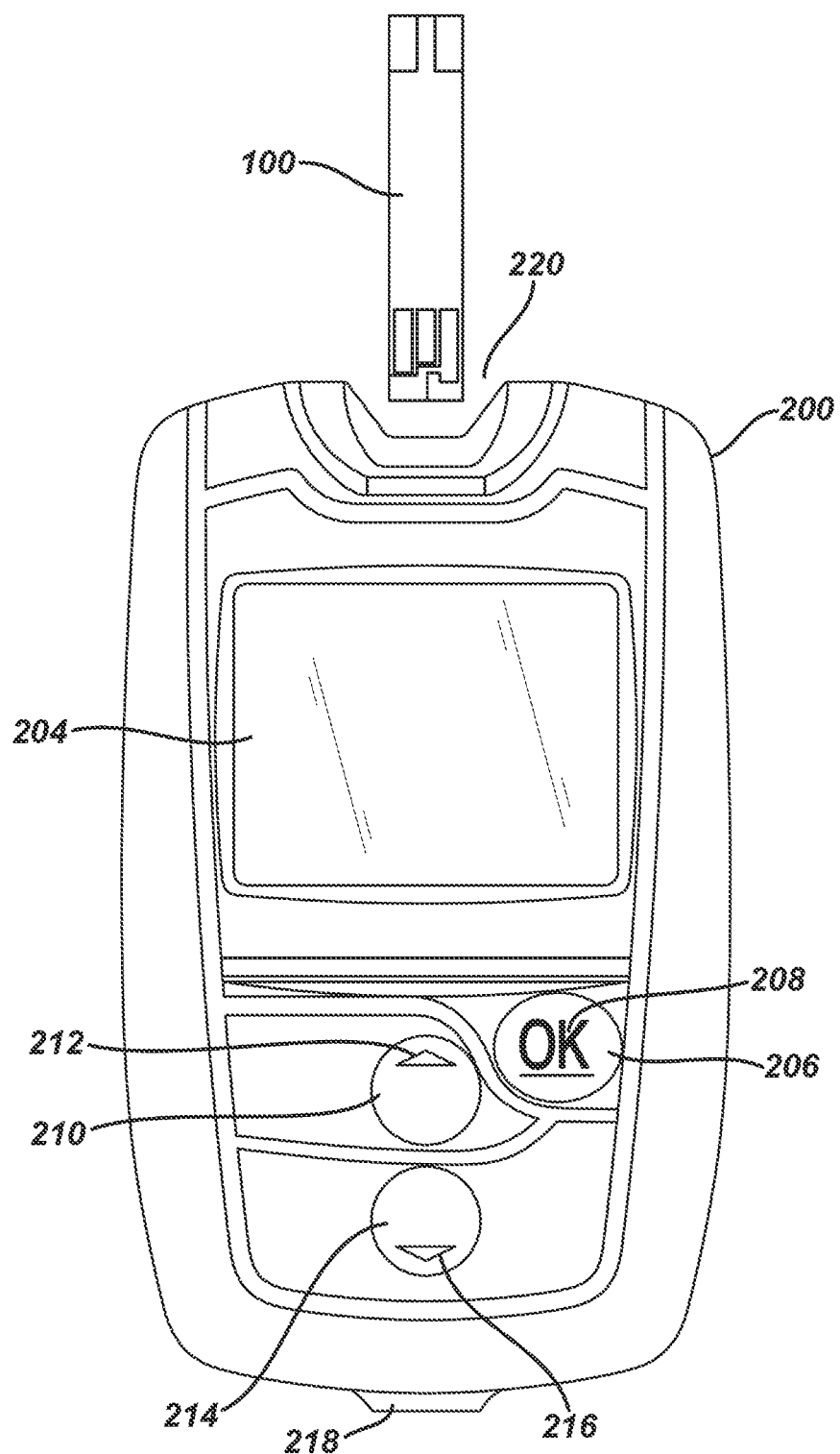
FIG. 1A illustrates an analyte measurement system including a meter and a biosensor.

FIG. 1A illustrates a test meter 200 for testing analyte (e.g., glucose) levels in the blood of an individual with a biosensor produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a biosensor 100 (or its variants) into a strip port connector 220, by pressing and briefly holding first user interface input 206, or by the detection of data traffic across a data port 218. Test meter 200 can be switched off by removing biosensor 100 (or its variants), pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the biosensor batches have a substantially uniform calibration characteristic. The calibration input can be a set of values ascribed to a particular biosensor batch. For example, the calibration input can include a batch "slope" value and a batch "intercept" value for a particular biosensor batch. The calibrations input, such as batch slope and intercept values, may be preset within the meter as will be described below.

Figure 2A:
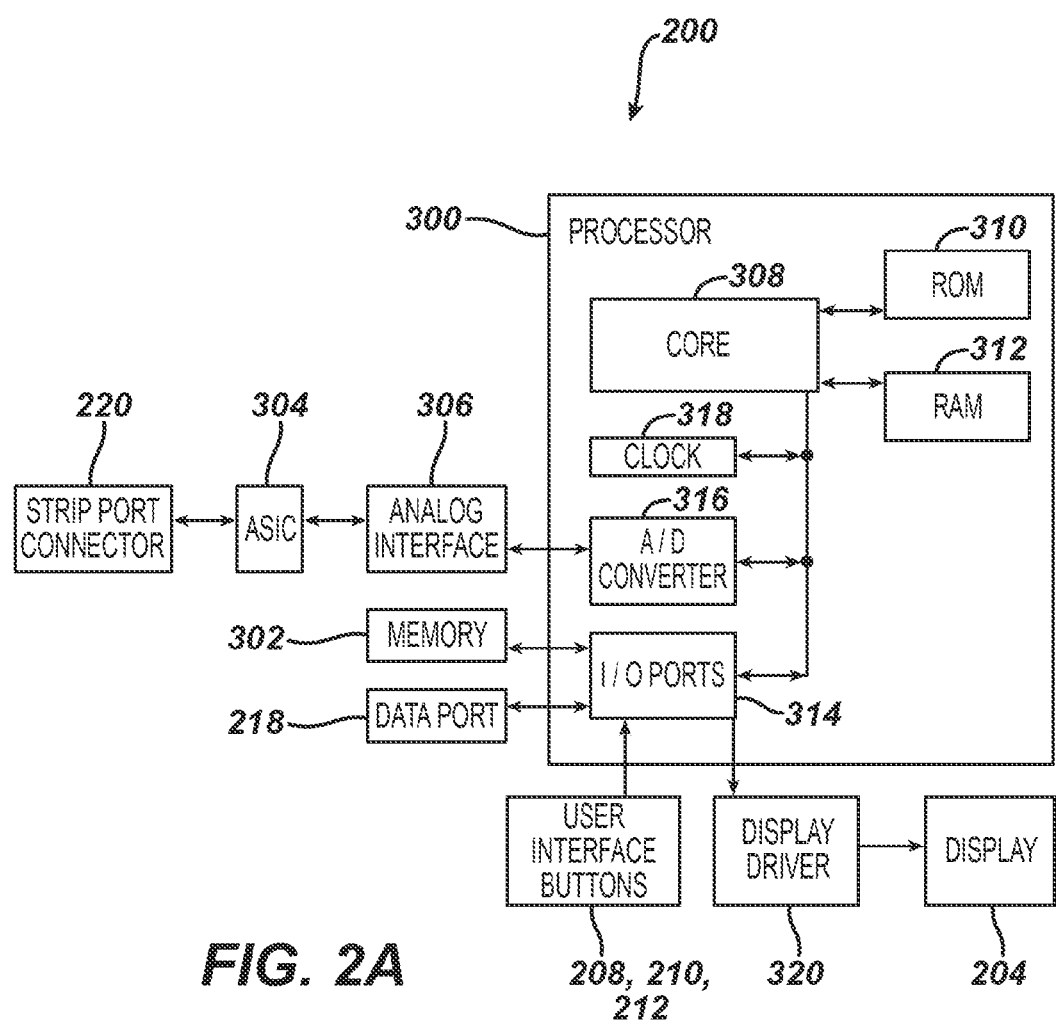
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 (or its variants) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006070200, which is hereby incorporated by reference into this application as if fully set forth herein.

Figure 1B:
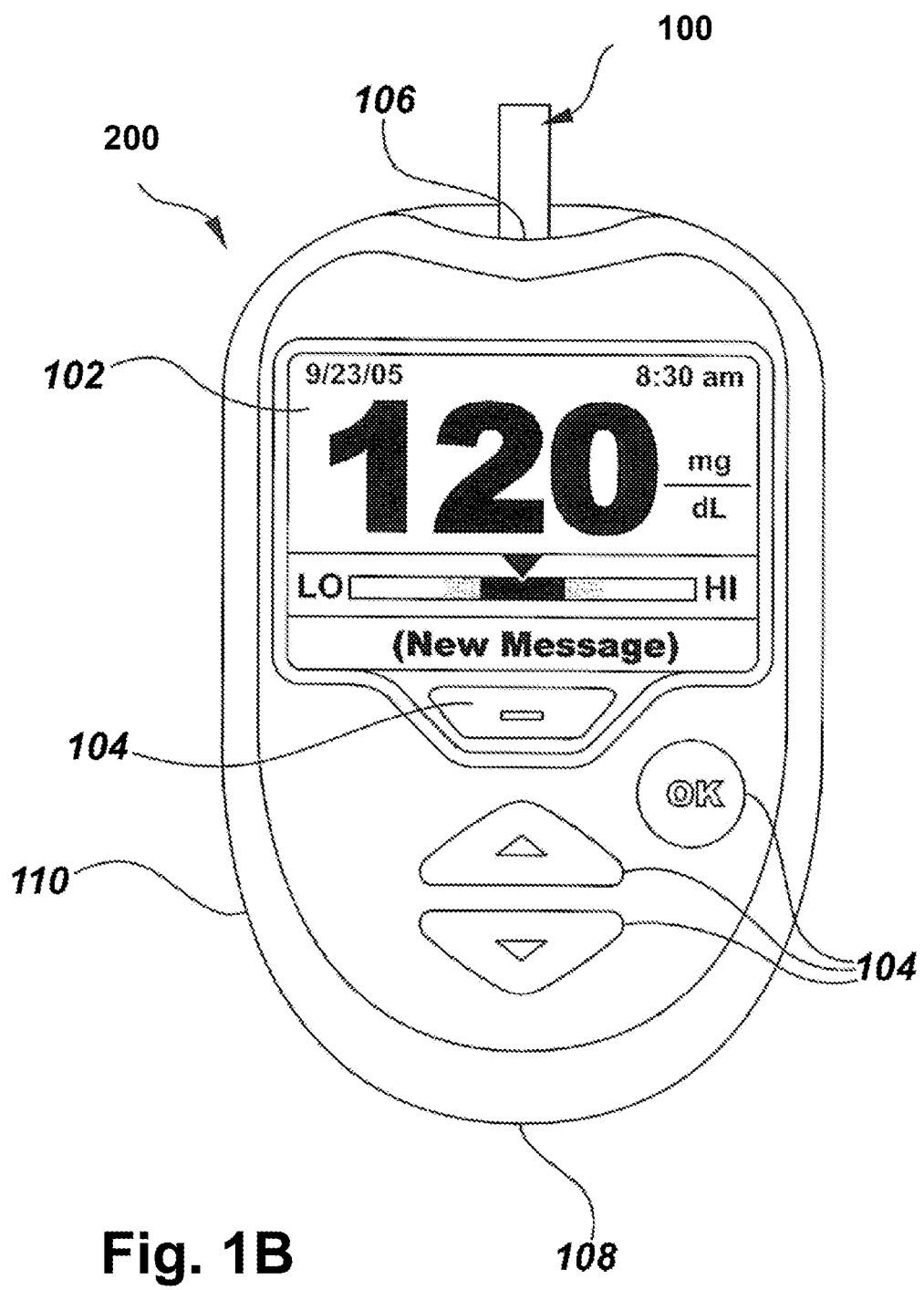
FIG. 1B illustrates yet another analyte measurement system including a meter and a biosensor.

Referring to FIG. 1B, another embodiment of a hand-held test meter 200 is provided. This version of the meter 200 includes a display 102, a plurality of user interface buttons 104, a strip port connector 106, a USB interface 108, and a housing. Referring to 2A-2D, the hand-held test meter 200 of FIGS. 1A and 1B also includes a microcontroller block 112, a physical characteristic measurement block 114, a display control block 116, a memory block 118 and other electronic components (not shown) for applying a test voltage to biosensor, and also for measuring an electrochemical response (e.g., plurality of test current values) and determining an analyte based on the electrochemical response. To simplify the current descriptions, the FIGURES do not depict all such electronic circuitry.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with a biosensor 100, such as an electrochemical-based biosensor configured for the determination of glucose in a whole blood sample. Therefore, the biosensor is configured for operative insertion into strip port connector 106 and to operatively interface with phase-shift-based hematocrit measurement block 114 via, for example, suitable electrical contacts.

USB Interface 108 can be any suitable interface known to one skilled in the art. USB Interface 108 is essentially a passive component that is configured to power and provide a data line to hand-held test meter 200.

Once a biosensor is interfaced with hand-held test meter 200, or prior thereto, a bodily fluid sample (e.g., a whole blood sample) is introduced into a sample chamber of the biosensor. The biosensor can include enzymatic reagents that selectively and quantitatively transform an analyte into another predetermined chemical form. For example, the biosensor can include an enzymatic reagent with ferricyanide and glucose oxidase so that glucose can be physically transformed into an oxidized form.

Memory block 118 of hand-held test meter 200 includes a suitable algorithm and can be configured, along with microcontroller block 112 to determine an analyte based on the electrochemical response of biosensor and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing and can include any suitable microcontroller and/or micro-processor known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (A/D) processing capabilities suitable for measuring voltages generated by phase shift based hematocrit measurement blocks employed in embodiments of the present disclosure.

Figure 2B:
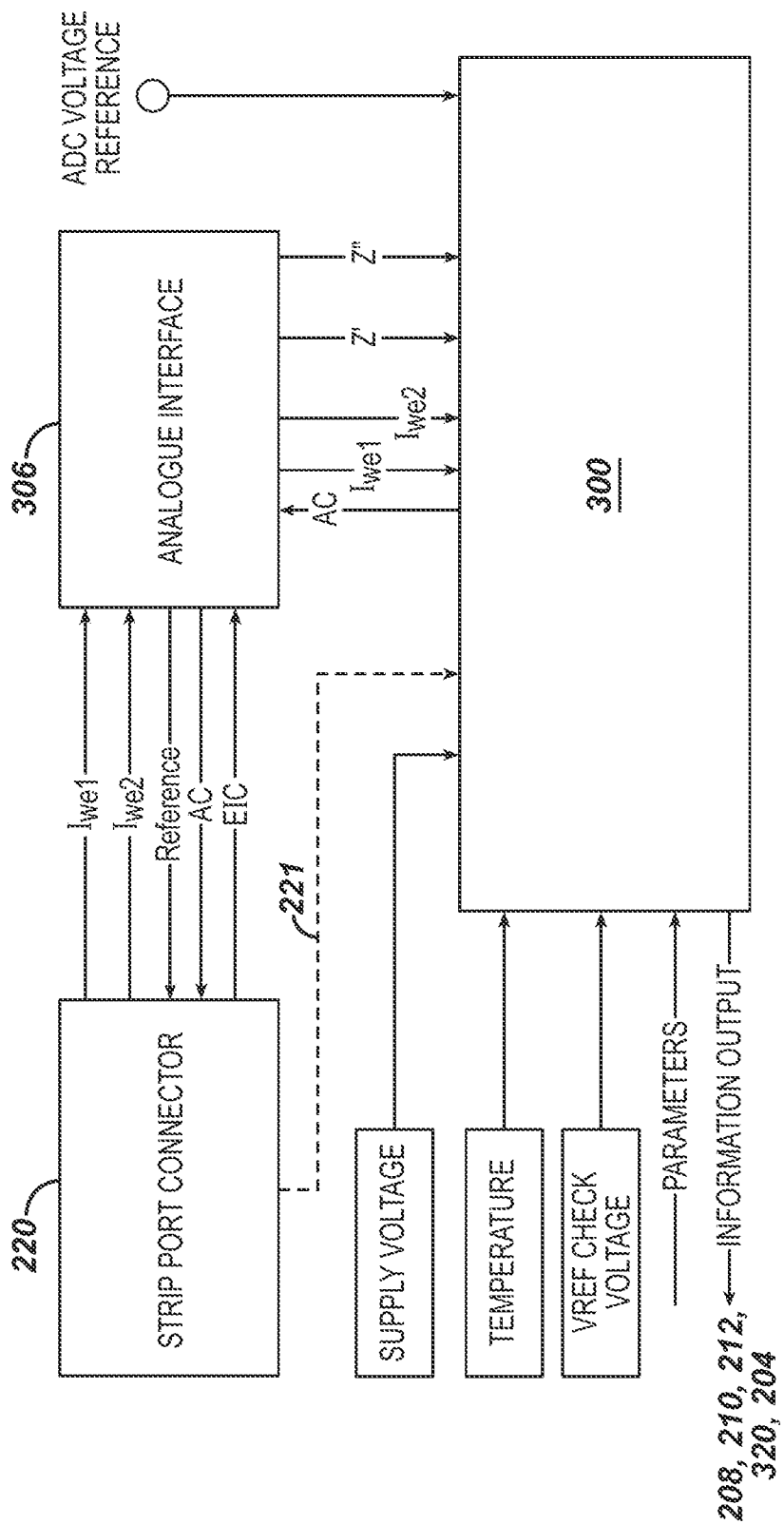
FIG. 2B illustrates in simplified schematic form a preferred implementation of a variation of meter 200.
Figure 2C:
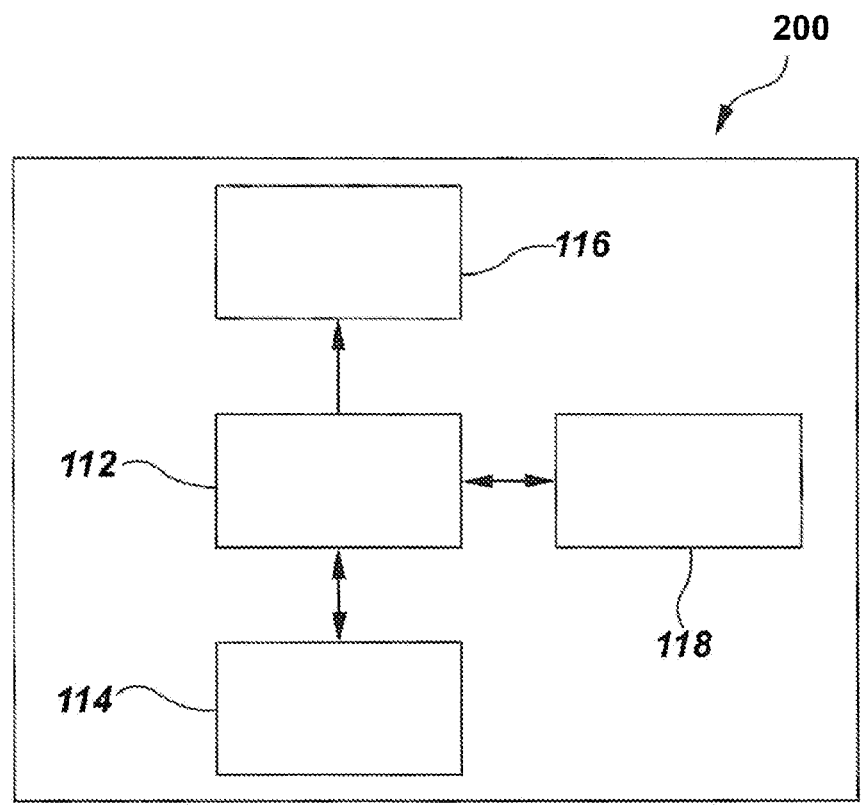
FIG. 2C is a simplified block diagram of various blocks of the hand-held test meter of FIGS. 1A and 1B.
Figure 2D:
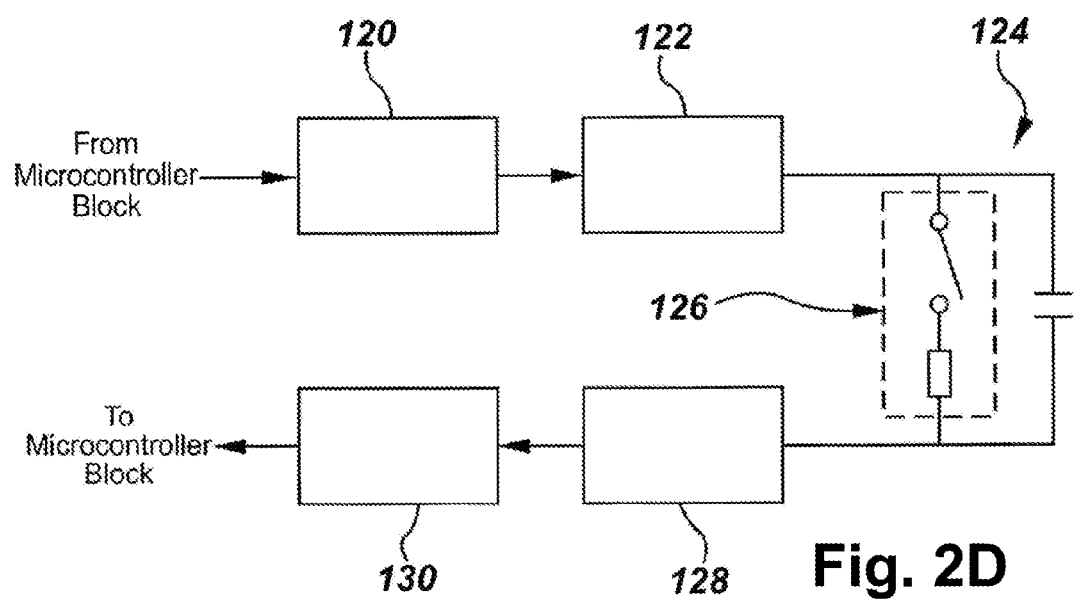
FIG. 2D is a simplified block diagram of a physical characteristic measurement block as can be employed in embodiments according to the present disclosure.

Referring in particular to FIG. 2D, phase-shift-based hematocrit measurement block 114 includes a signal generation sub-block 120, a low pass filter sub-block 122, an biosensor sample cell interface sub-block 124, an optional calibration load block 126 (within the dashed lines of FIG. 2D), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of an biosensor inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

It has been determined that a relationship exists between the reactance of a whole blood sample and the hematocrit of that sample. Electrical modeling of a bodily fluid sample (i.e., a whole blood sample) as parallel capacitive and resistive components indicates that when an alternating current (AC) signal is forced through the bodily fluid sample, the phase shift of the AC signal will be dependent on both the frequency of the AC voltage and the hematocrit of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz, and preferably about 75 kHz. Therefore, the hematocrit of a bodily fluid sample can be measured by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Figure 3A:
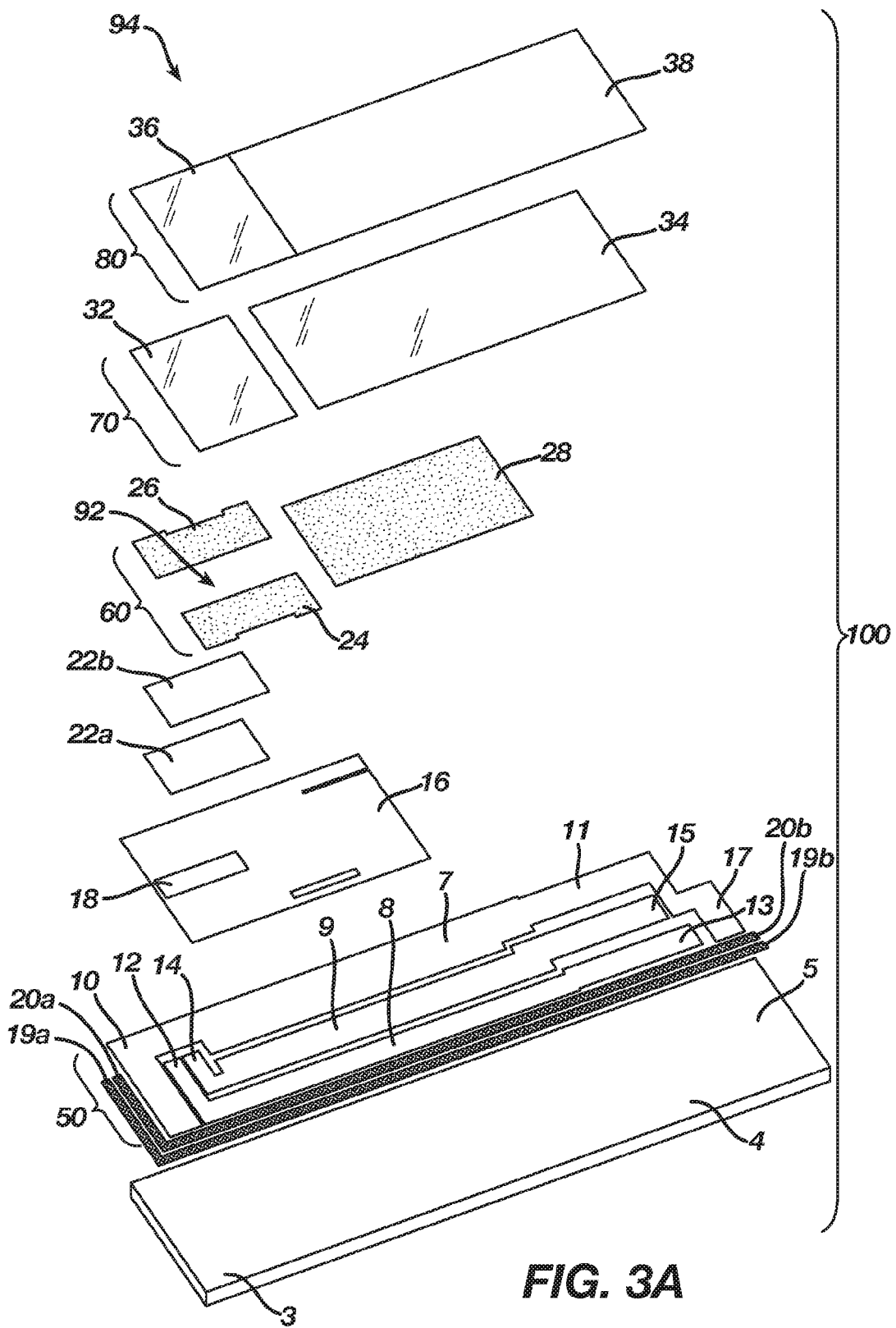
FIG. 3A illustrates the test strip 100 of the system of FIG. 1 in which there are two physical characteristic sensing electrodes upstream of the measurement electrodes.

FIG. 3A is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Figure 3B:
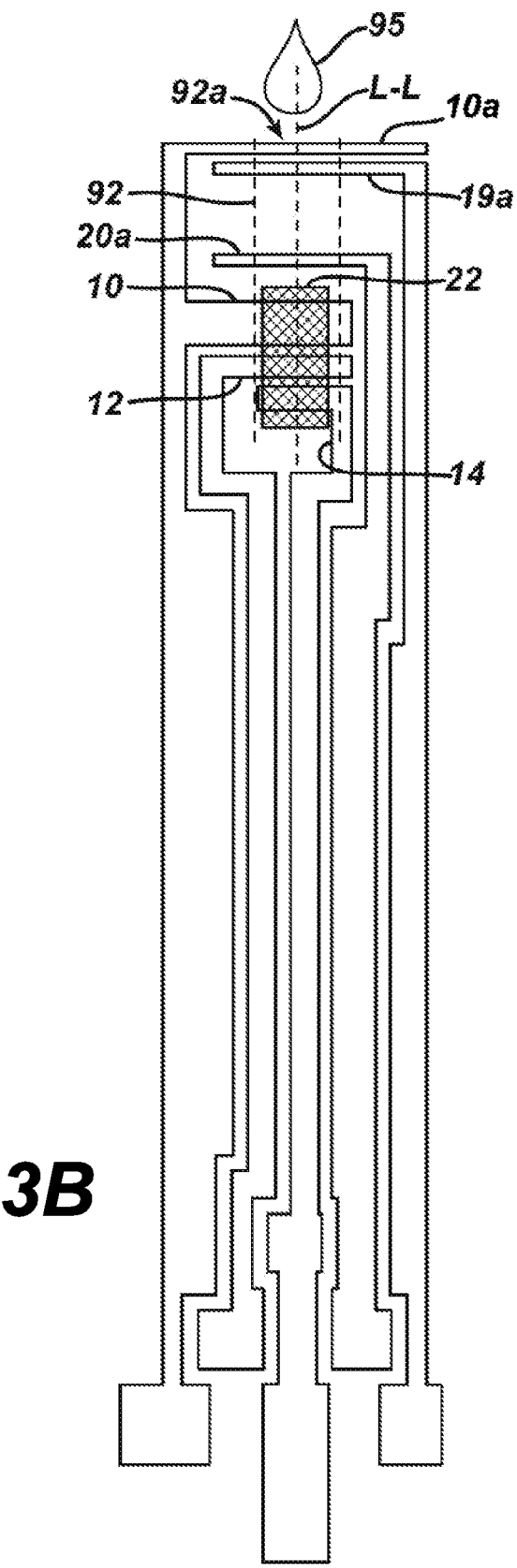
FIG. 3B illustrates a variation of the test strip of FIG. 3A in which a shielding or grounding electrode is provided for proximate the entrance of the test chamber.

Test strip 100 may include a sample-receiving chamber 92 through which a physiological fluid sample 95 may be drawn through or deposited (FIG. 3B). The physiological fluid sample discussed herein may be blood. Sample-receiving chamber 92 can include an inlet at a proximal end and an outlet at the side edges of test strip 100, as illustrated in FIG. 3A. A fluid sample 95 can be applied to the inlet along axis L-L (FIG. 3B) to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A. For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A, first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A.

In the embodiment of FIG. 3B which is a variation of the test strip of FIG. 3A, an additional electrode 10a is provided as an extension of any of the plurality of electrodes 19a, 20a, 14, 12, and 10. It must be noted that the built-in shielding or grounding electrode 10a is used to reduce or eliminate any capacitance coupling between the finger or body of the user and the characteristic measurement electrodes 19a and 20a. The grounding electrode 10a allows for any capacitance to be directed away from the sensing electrodes 19a and 20a. To do this, the grounding electrode 10a can be connected any one of the other five electrodes or to its own separate contact pad (and track) for connection to ground on the meter instead of one or more of contact pads 15, 17, 13 via respective tracks 7, 8, and 9. In a preferred embodiment, the grounding electrode 10a is connected to one of the three electrodes that has reagent 22 disposed thereon. In a most preferred embodiment, the grounding electrode 10a is connected to electrode 10. Being the grounding electrode, it is advantageous to connect the grounding electrode to the reference electrode (10) so not to contribute any additional current to the working electrode measurements which may come from background interfering compounds in the sample. Further by connecting the shield or grounding electrode 10a to electrode 10 this is believed to effectively increase the size of the counter electrode 10 which can become limiting especially at high signals. In the embodiment of FIG. 3B, the reagent are arranged so that they are not in contact with the measurement electrodes 19a and 20a. Alternatively, the reagent 22 can be arranged so that the reagent 22 contacts at least one of the sensing electrodes 19a and 20a.

Figure 3C:
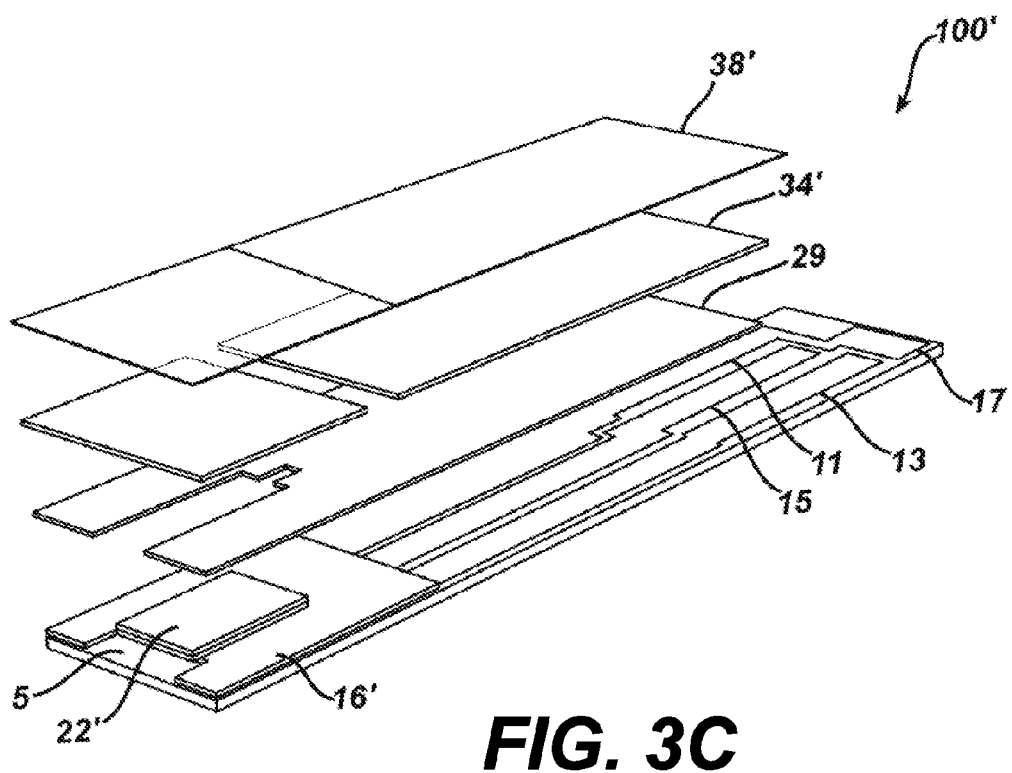
FIG. 3C illustrates a variation of test strip 100 of FIGS. 3A and 3B in which certain components of the test strip have been integrated together into a single unit.

In alternate version of test strip 100, shown here in FIG. 3C, the top layer 38, hydrophilic film layer 34 and spacer 29 have been combined together to form an integrated assembly for mounting to the substrate 5 with reagent layer 22' disposed proximate insulation layer 16'.

In the embodiment of FIG. 3B, the analyte measurement electrodes 10, 12, and 14 are disposed in generally the same configuration as in FIG. 3A. The electrodes 19a and 20a to sense physical characteristic (e.g., hematocrit) level, however, are disposed in a spaced apart configuration in which one electrode 19a is proximate an entrance 92a to the test chamber 92 and another electrode 20a is at the opposite end of the test chamber 92. Electrodes 10, 12, and 14 are disposed to be in contact with a reagent layer 22 whereas the electrodes 19a and 20a are not in contact with the reagent.

In FIGS. 3A-3C, the physical characteristic (e.g., hematocrit) sensing electrodes 19a and 20a are disposed adjacent each other and may be placed at the opposite end 92b of the entrance 92a to the test chamber 92 (FIGS. 3C and 3D) or adjacent the entrance 92a (not shown for brevity). In all of these embodiments, the physical characteristic sensing electrodes are spaced apart from the reagent layer 22 so that these physical characteristic sensing electrodes are not impacted by the electrochemical reaction of the reagent in the presence of a fluid sample (e.g., blood, control solution or interstitial fluid) containing glucose.

In the various embodiments of the biosensor, there are two measurements that are made to a fluid sample deposited on the biosensor. One measurement is that of the concentration of the analyte (e.g. glucose) in the fluid sample while the other is that of physical characteristic (e.g., hematocrit) in the same sample. The measurement of the physical characteristic (e.g., hematocrit) is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. Each measurement is discussed in detail as follow with respect to FIGS. 4A, 4B and 5.

Figure 4A:
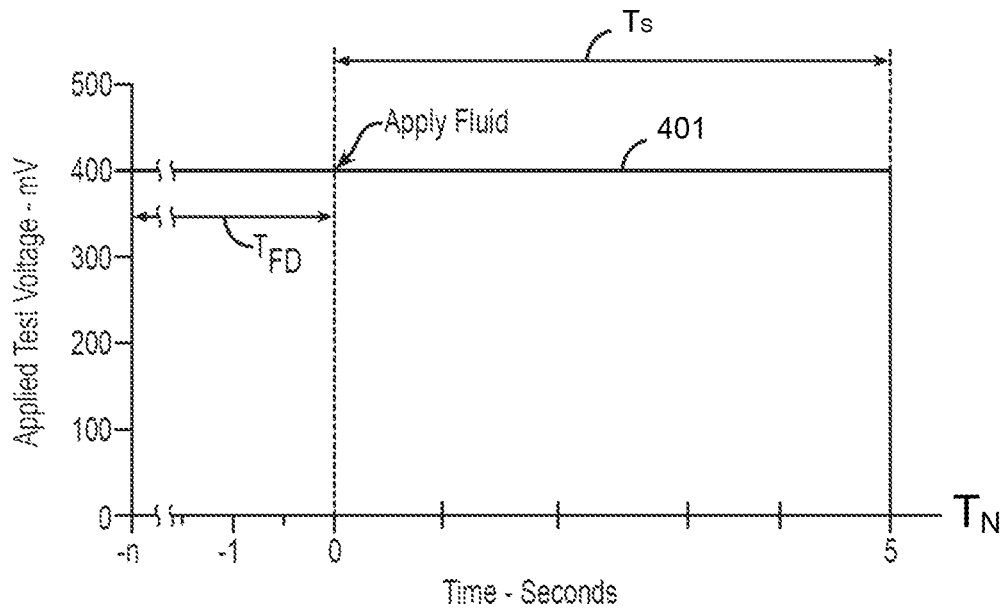
FIG. 4A illustrates a graph of time over applied potential to the biosensor of FIG. 3A, 3B or 3C.

FIG. 4A is an exemplary chart of a test signal applied to test strip 100 and its variations shown here in FIGS. 3A-3C. Before a fluid sample is applied to test strip 100 (or its variants), test meter 200 is in a fluid detection mode in which a first test signal of about 400 millivolts is applied between second working electrode and reference electrode. A second test signal of about 400 millivolts is preferably applied simultaneously between first working electrode (e.g., electrode 12 of strip 100) and reference electrode (e.g., electrode 10 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants) such that the fluid wets either the first working electrode 12 or second working electrode 14 (or both working electrodes) with respect to reference electrode 10. Once test meter 200 recognizes that the physiological fluid has been applied because of, for example, a sufficient increase in the measured test current at either or both of first working electrode 12 and second working electrode 14, test meter 200 assigns a zero second marker at zero time "0" and starts the test time interval $T_S$. Test meter 200 may sample the current transient output at a suitable sampling rate, such as, for example, every 1 milliseconds to every 100 milliseconds. Upon the completion of the test time interval $T_S$, the test signal is removed. For simplicity, FIG. 4A only shows the first test signal applied to test strip 100 (or its variants).

Hereafter, a description of how analyte (e.g., glucose) concentration is determined from the known signal transients (e.g., the measured electrical signal response in nanoamperes as a function of time) that are measured when the test voltages of FIG. 4A are applied to the test strip 100 (or its variants).

Figure 4B:
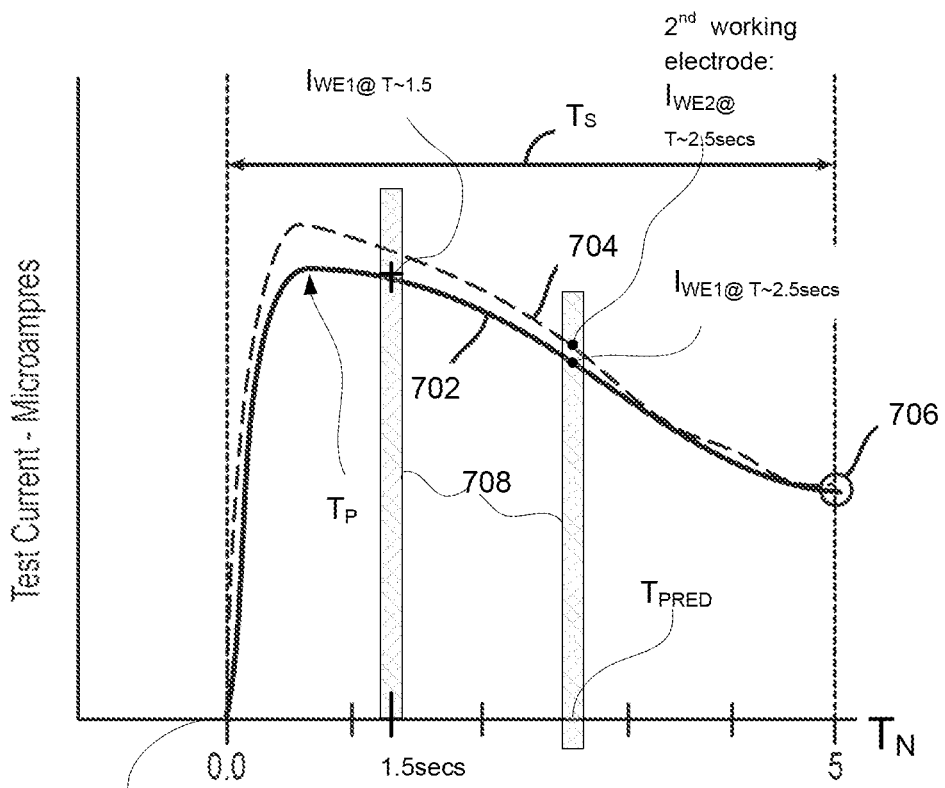
FIG. 4B illustrates a graph of time over output current from the biosensor of FIG. 3A, 3B or 3C.

In FIG. 4A, the first and second test voltages applied to test strip 100 (or its variants described herein) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to time $t_0$. As the voltage 401 is maintained in FIG. 4A for the duration of $T_S$, output signals are generated, shown here in FIG. 4B with the current transient 702 for the first working electrode 12 being generated starting at zero time and likewise the current transient 704 for the second working electrode 14 is also generated with respect to the zero time. It is noted that while the signal transients 702 and 704 have been placed on the same referential zero point for purposes of explaining the process, in physical term, there is a slight time differential between the two signals due to fluid flow in the chamber towards each of the working electrodes 12 and 14 along axis L-L. However, the current transients are sampled and configured in the microcontroller to have the same start time. In FIG. 4B, the current transients build up to a peak proximate peak time Tp at which time, the current slowly drops off until approximately one of 2.5 seconds or 5 seconds after zero time. At the point 706, approximately at 5 seconds, the output signal for each of the working electrodes 12 and 14 may be measured and added together. Alternatively, the signal from only one of the working electrodes 12 and 14 can be doubled.

Referring back to FIG. 2B, the system drives a signal to measure or sample the output signals $I_E$ from at least one the working electrodes (12 and 14) at any one of a plurality of time points or positions $T_1, T_2, T_3 \ldots TN$. As can be seen in FIG. 4B, the time position can be any time point or interval in the test sequence $T_S$. For example, the time position at which the output signal is measured can be a single time point $T_{1.5}$ at 1.5 seconds or an interval 708 (e.g., interval-10 milliseconds or more depending on the sampling rate of the system) overlapping the time point $T_{2.8}$ proximate 2.8 seconds.

From knowledge of the parameters of the biosensor (e.g., batch calibration code offset and batch slope) for the particular test strip 100 and its variations, the analyte (e.g., glucose) concentration can be calculated. Output transient 702 and 704 can be sampled to derive signals $I_E$ (by summation of each of the current $I_{WE1}$ and $I_{WE2}$ or doubling of one of $I_{WE1}$ or $I_{WE2}$) at various time positions during the test sequence. From knowledge of the batch calibration code offset and batch slope for the particular test strip 100, the analyte (e.g., glucose) concentration can be calculated.

It is noted that "Intercept" and "Slope" are the values obtained by measuring calibration data from a batch of biosensors. Typically around 1500 biosensors are selected at random from the lot or batch. Physiological fluid (e.g., blood) from donors is spiked to various analyte levels, typically six different glucose concentrations. Typically, blood from 12 different donors is spiked to each of the six levels. Eight biosensors (or strips in this embodiment) are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope m and batch intercept c for the remaining strips from the lot or batch. The applicants have also provided methods and systems in which the batch slope is derived during the determination of an analyte concentration. The "batch slope", or "Slope", may therefore be defined as the measured or derived gradient of the line of best fit for a graph of measured glucose concentration plotted against actual glucose concentration (or measured current versus YSI current). The "batch intercept", or "Intercept", may therefore be defined as the point at which the line of best fit for a graph of measured glucose concentration plotted against actual glucose concentration (or measured current versus YSI current) meets the y axis.

The various components, systems and procedures described earlier allow for applicant to provide an analyte measurement system. In particular, this system includes a biosensor that has a substrate and a plurality of electrodes connected to respective electrode connectors. The system further includes an analyte meter 200 that has a housing, a test strip port connector configured to connect to the respective electrode connectors of the test strip, and a microcontroller 300, shown here in FIG. 2B. The microcontroller 300 is in electrical communication with the test strip port connector 220 to apply electrical signals or sense electrical signals from the plurality of electrodes.

Referring to FIG. 2B, details of a preferred implementation of meter 200 where the same numerals in FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and signal sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) signal sampled or measured from working electrode 1 of the biosensor or $I_{we1}$; (4) signal sampled or measured from working electrode 2 of the biosensor or $I_{we2}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z" where:

$$P=\tan^{-1}\{Z''/Z'\} \qquad \text{Eq. 3.1}$$

and magnitude M (in ohms and conventionally written as |Z|) from line Z' and Z" of the interface 306 can be determined where $$M=\sqrt{(Z')^2+(Z'')^2} \qquad \text{Eq. 3.2}$$

In this system, the microprocessor is configured to: (a) apply a first signal to the plurality of electrodes so that a batch slope defined by a physical characteristic of a fluid sample is derived and (b) apply a second signal to the plurality of electrodes so that an analyte concentration is determined based on the derived batch slope. For this system, the plurality of electrodes of the test strip or biosensor includes at least two electrodes to measure the physical characteristic and at least two other electrodes to measure the analyte concentration. For example, the at least two electrodes and the at least two other electrodes are disposed in the same chamber provided on the substrate. Alternatively, the at least two electrodes and the at least two other electrodes are disposed in respective two different chambers provided on the substrate. It is noted that for some embodiments, all of the electrodes are disposed on the same plane defined by the substrate. In particular, in some of the embodiments described herein, a reagent is disposed proximate to the at least two other electrodes and no reagent is disposed on the at least two electrodes. One feature of note in this system is the ability to provide for an accurate analyte measurement within about 10 seconds of deposition of a fluid sample (which may be a physiological sample) onto the biosensor as part of the test sequence.

As an example of an analyte calculation (e.g., glucose) for strip 100 (FIGS. 3A-3C), it is assumed in FIG. 4B that the sampled signal value at 706 for the first working electrode 12 is about 1600 nanoamperes whereas the signal value at 706 for the second working electrode 14 is about 1300 nanoamperes and the calibration code of the test strip indicates that the Intercept is about 500 nanoamperes and the Slope is about 18 nanoamperes/mg/dL. Glucose concentration $G_0$ can be thereafter be determined from Equation 3.3 as follow:

$$G_0 = [(I_E) - \text{Intercept}]/\text{Slope} \qquad \text{Eq. 3.3}$$

where
- $I_E$ is a signal (proportional to analyte concentration) which is the total signal from all of the electrodes in the biosensor (e.g., for sensor 100, both electrodes 12 and 14 (or $I_{we1} + I_{we2}$));
- $I_{we1}$ is the signal measured for the first working electrode at the set sampling time;
- $I_{we2}$ is the signal measured for the second working electrode at the set sampling time;
- Slope is the value obtained from calibration testing of a batch of test strips of which this particular strip comes from;
- Intercept is the value obtained from calibration testing of a batch of test strips of which this particular strip comes from.

From Eq. 3.3; $G_0 = [(1600+1300)-500]/18$ and therefore, $G_0 = 133.33$ nanoamp~133 mg/dL.

It is noted here that although the examples have been given in relation to a biosensor 100 which has two working electrodes (12 and 14 in FIG. 3A) such that the measured currents from respective working electrodes have been added together to provide for a total measured current $I_E$, the signal resulting from only one of the two working electrodes can be multiplied by two in a variation of test strip 100 where there is only one working electrode (either electrode 12 or 14). Instead of a total signal, an average of the signal from each working electrode can be used as the total measured current $I_E$ for Equations 3.3, 6, and 5-7 described herein, and of course, with appropriate modification to the operational coefficients (as known to those skilled in the art) to account for a lower total measured current $I_E$ than as compared to an embodiment where the measured signals are added together. Alternatively, the average of the measured signals can be multiplied by two and used as $I_E$ in Equations 3.3, 6, and 5-7 without the necessity of deriving the operational coefficients as in the prior example. It is noted that the analyte (e.g., glucose) concentration here is not corrected for any physical characteristic (e.g., hematocrit value) and that certain offsets may be provided to the signal values $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Now that an analyte (e.g., glucose) concentration (Go) can be determined from the signal $I_E$, a description of applicant's technique to determine the physical characteristic (e.g., hematocrit) of the fluid sample is provided hereafter. Specifically, the system 200 (FIGS. 2a and 2b) applies a first oscillating input signal at a first frequency (e.g., of about 25-500 kilo-Hertz) to a pair of sensing electrodes. The system is also set up to measure or detect a first oscillating output signal 802 from the third and fourth electrodes, which in particular involve measuring a first time differential $\Delta t_1$ between the first input and output oscillating signals. At the same time or during overlapping time durations, the system may also apply a second oscillating input signal (not shown for brevity) at a second frequency (e.g., about 100 kilo-Hertz to about 1 MegaHertz or higher, and preferably about 250 kilo Hertz) to a pair of electrodes and then measure or detect a second oscillating output signal from the third and fourth electrodes, which may involve measuring a second time differential $\Delta t_2$ (not shown) between the first input and output oscillating signals. From these signals, the system estimates a physical characteristic (e.g., hematocrit) of the fluid sample based on the first and second time differentials $\Delta t_1$ and $\Delta t_2$. Thereafter, the system is able to derive a glucose concentration. The estimate of the physical characteristic (e.g., hematocrit) can be done by applying an equation of the form $$HCT_{EST} = \frac{(C_1 \Delta t_1 - C_2 \Delta t_2 - C_3)}{m_1} \qquad \text{Eq. 4.1}$$

where
each of $C_1$, $C_2$, and $C_3$ is an operational constant for the test strip and $m_1$ represent a parameter from regressions data.

Details of this exemplary technique can be found in Provisional U.S. patent application Ser. No. 61/530,795 filed on Sep. 2, 2011, entitled, "Hematocrit Corrected Glucose Measurements for Electrochemical Test Strip Using Time Differential of the Signals", which is hereby incorporated by reference.

Another technique to determine physical characteristic (e.g., hematocrit) can be by two independent measurements of physical characteristic (e.g., hematocrit). This can be obtained by determining: (a) the impedance of the fluid sample at a first frequency and (b) the phase angle of the fluid sample at a second frequency substantially higher than the first frequency. In this technique, the fluid sample is modeled as a circuit having unknown reactance and unknown resistance. With this model, an impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art. Details of this technique is shown and described in pending provisional patent application Ser. No. 61/530,808 filed Sep. 2, 2011, which is incorporated by reference. Other suitable techniques for determining the physical characteristic (e.g., hematocrit, viscosity, temperature or density) of the fluid sample can also be utilized such as, for example, U.S. Pat. No. 4,919,770, U.S. Pat. No. 7,972,861, US Patent Application Publication Nos. 2010/0206749, 2009/0223834, or "Electric Cell-Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi: 10.1006/excr.2000.4919, available online at http://www.idealibrary.com1; "Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. Vol. 80, No. 1, 158-165 (2007), all of these documents are incorporated by reference.

Another technique to determine the physical characteristic (e.g., hematocrits, density, or temperature) can be obtained by knowing the phase difference (e.g., phase angle) and magnitude of the impedance of the sample. In one example, the following relationship is provided for the estimate of the physical characteristic or impedance characteristic of the sample ("IC"):

$$IC = M^2 \cdot y_1 + M \cdot y_2 + y_3 + P^2 \cdot y_4 + P \cdot y_5 \qquad \text{Eq. 4.2}$$

where:
M represents a magnitude |Z| of a measured impedance in ohms);
P represents a phase difference between the input and output signals (in degrees)
$y_1$ is about −3.2e-08 and ±10%, 5% or 1% of the numerical value provided hereof (and depending on the frequency of the input signal, can be zero);
$y_2$ is about 4.1e-03 and ±10%, 5% or 1% of the numerical value provided hereof (and depending on the frequency of the input signal, can be zero);
$y_3$ is about −2.5+01 and ±10%, 5% or 1% of the numerical value provided hereof;
$y_4$ is about 1.5e-01 and ±10%, 5% or 1% of the numerical value provided hereof (and depending on the frequency of the input signal, can be zero); and
$y_5$ is about 5.0 and ±10%, 5% or 1% of the numerical value provided hereof (and depending on the frequency of the input signal, can be zero).

It is noted here that where the frequency of the input AC signal is high (e.g., greater than 75 kHz) then the parametric terms $y_1$ and $y_2$ relating to the magnitude of impedance M may be ±200% of the exemplary values given herein such that each of the parametric terms may include zero or even a negative value. On the other hand, where the frequency of the AC signal is low (e.g., less than 75 kHz), the parametric terms $y_4$ and $y_5$ relating to the phase angle P may be ±200% of the exemplary values given herein such that each of the parametric terms may include zero or even a negative value. It is noted here that a magnitude of H or HCT, as used herein, is generally equal to the magnitude of IC. In one exemplary implementation, H or HCT is equal to IC as H or HCT is used herein this application.

In another alternative implementation, Equation 4.3 is provided. Equation 4.3 is the exact derivation of the quadratic relationship, without using phase angles as in Equation 4.2.

$$IC = \frac{-y_2 + \left|\sqrt{y_2^2 - (4y_3(y_1 - M))}\right|}{2y_1} \qquad \text{Eq. 4.3}$$

where:
IC is the Impedance Characteristic [%];
M is the magnitude of impedance [Ohm];
$y_1$ is about 1.2292e1 and ±10%, 5% or 1% of the numerical value provided hereof;
$y_2$ is about −4.3431e2 and ±10%, 5% or 1% of the numerical value provided hereof;
$y_3$ is about 3.5260e4 and ±10%, 5% or 1% of the numerical value provided hereof.

Figure 5:
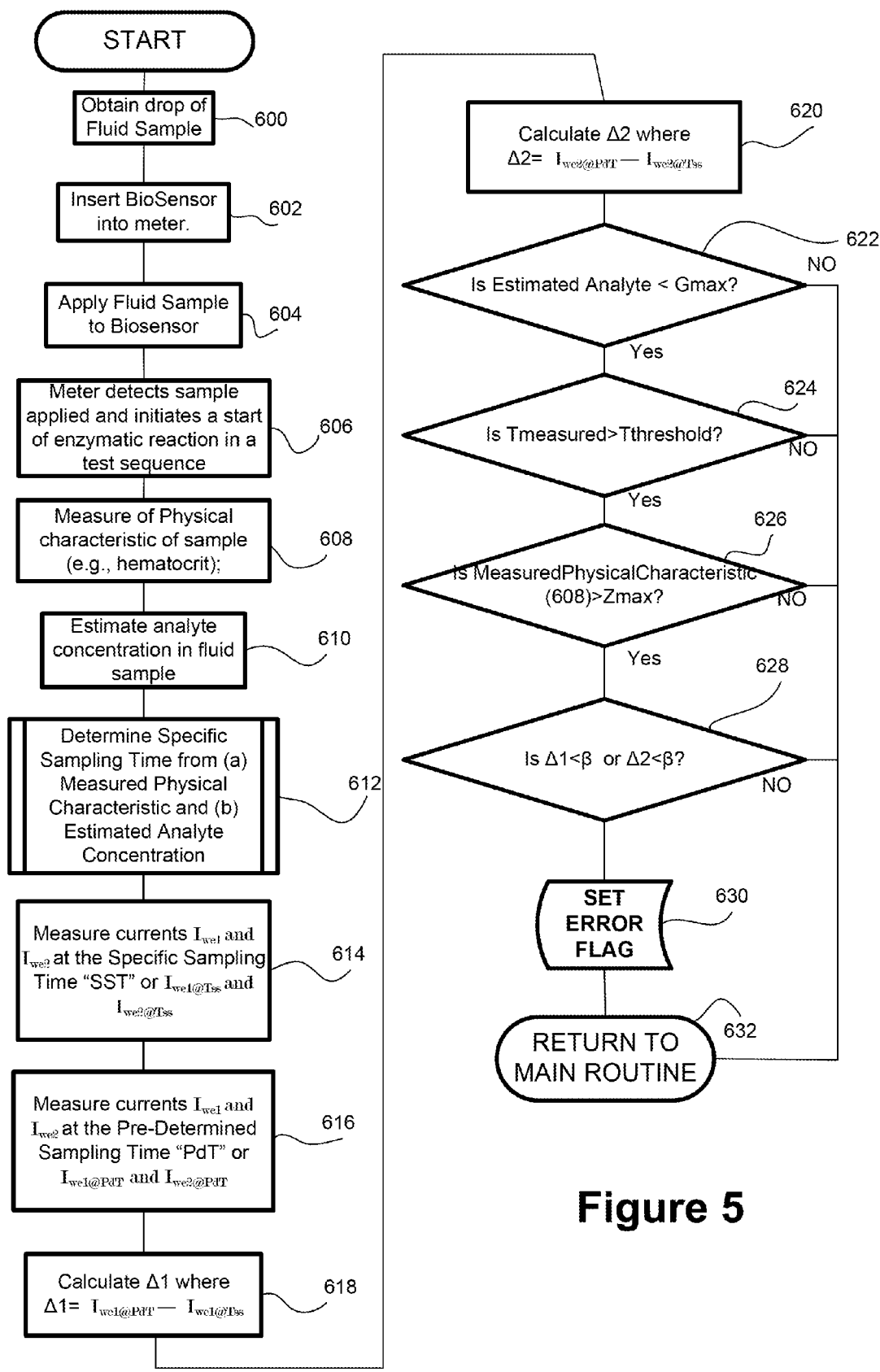
FIG. 5 illustrates a logical flow chart to determine error in the waveform output signal transients of the analyte measurements.

By virtue of the various components, systems and insights provided herein, a technique to detect error caused by a defect on the reference or counter electrode during analyte measurement can be understood with reference to FIG. 5. This technique involves depositing a fluid sample (which may be a physiological sample or a control solution sample) on a biosensor at step 604 (e.g., in the form of a test strip as show in FIGS. 3A-3C) that has been inserted into a meter (step 602). Once the meter 200 is turned on, a signal is applied to the strip 100 (or its variants) and when the sample is deposited onto the test chamber, the applied signal physically transforms the analyte (e.g., glucose) in the sample into a different physical form (e.g., gluconic acid) due to the enzymatic reaction of the analyte with the reagent in the test chamber. As the sample flows into the capillary channel of the test cell, at least one physical characteristic of the sample is obtained from an output of another signal driven into the sample (step 608) along with estimate of the analyte concentration (step 610). From the obtained physical characteristic (step 608) and estimated analyte concentration (step 610), a sampling time slot is defined (at step 612) at which the signal output from the sample during the test sequence is measured (at step 614) and used for calculating the analyte concentration in a main routine. In particular, the step of obtaining the physical characteristic (step 608) may include applying a first signal to the sample to measure a physical characteristic of the sample, while the step 606 of initiating an enzymatic reaction may involve driving a second signal to the sample, and the step of measuring (step 614) may entail evaluating an output signal from the at least two electrodes at a point in time after the start of the test sequence, in which the point in time is set (at step 612) as a function of at least the measured or estimated physical characteristic (step 608) and estimated analyte concentration (step 610).

The determination of the appropriate point (or time interval) during the test sequence $T_S$ as a function of the measured or estimated physical characteristic(s) (in step 612) can be determined by the use of a look-up table programmed into the microprocessor of the system. For example, a look-up table may be provided that allows for the system to select the appropriate sampling time for the analyte (e.g., glucose or ketone) with measured or known physical characteristic (e.g., hematocrit or viscosity) of the sample.

In particular, an appropriate sampling time point may be based on an early estimation of the analyte and the measured or known physical characteristic to arrive at the appropriate sampling time that gives the lowest error or bias as compared to referential values. In this technique, a look up table is provided in which the defined sampling time point is correlated to (a) the estimated analyte concentration and (b) the physical characteristic of the sample. For example, Table 1 may be programmed into the meter to provide a matrix in which qualitative categories (low, medium, and high glucose) of the estimated analyte form the main column and the qualitative categories (low, medium, and high) of the measured or estimated physical characteristic form the header row. In the second column, t/Hct is a value determined experimentally of the time shift per % hematocrit difference from nominal hematocrit of 42%. As one example, for 55% hematocrit at "Mid-Glucose" would indicate a time shift of (42−55)*90=−1170 ms. The time of −1170 milliseconds is added to the original test time of about 5000 milliseconds giving (5000−1170=3830 milliseconds)~3.9 seconds.

TABLE 1

| Estimated Analyte | t/Hct (in milliseconds) | Specific Sampling Time $T_{SS}$ for Lo Hct (from start of test sequence, in seconds) | Specific Sampling Time $T_{SS}$ for Mid Hct (from start of test sequence, in seconds) | Specific Sampling Time $T_{SS}$ for High Hct (from start of test sequence, in seconds) |
| --- | --- | --- | --- | --- |
| Lo-Glucose | 40 | 5.5 | 5 | 4.5 |
| Mid-Glucose | 90 | 6.1 | 5 | 3.9 |
| Hi-Glucose | 110 | 6.3 | 5 | 3.6 |

The time $T_{SS}$ (i.e., a specified sampling time) at which the system should be sampling or measuring the output signal of the biosensor is based on both the qualitative category of the estimated analyte and measured or estimated physical characteristic and is predetermined based on regression analysis of a large sample size of actual physiological fluid samples. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. By sampling the entire signal output transient during the test sequence, the system can perform all of the needed calculations near the end of the test sequence rather than attempting to synchronize the sampling time with the set time point, which may introduce timing errors due to system delay.

Applicant hereafter will discuss the look-up Table 1 in relation to the particular analyte of glucose in physiological fluid samples. Qualitative categories of blood glucose are defined in the first column of Table 1 in which low blood glucose concentrations of less than about 70 mg/dL are designated as "Lo-Glucose"; blood glucose concentrations of higher than about 70 mg/dL but less than about 250 mg/dL are designated as "Mid-Glucose"; and blood glucose concentrations of higher than about 250 mg/dL are designated as "Hi-Glucose".

During a test sequence, an "Estimated Analyte" can be obtained by sampling the signal at a convenient time point, typically at five seconds during a typical 10 seconds test sequence. The measurement sampled at this five second time point (hereafter "Tes") allows for an accurate estimate of the analyte (in this case blood glucose). The system may then refer to a look-up table (e.g., Table 1) to determine when to measure the signal output from the test chamber at a specified sampling time $T_{SS}$ based on two criteria: (a) estimated analyte at Tes and (b) qualitative value of the physical characteristic of the sample. For criteria (b), the qualitative value of the physical characteristic is broken down into three sub-categories of Low Hct, Mid Hct and High Hct. Thus, in the event that the measured or estimated physical characteristic (e.g., hematocrit) is high (e.g., greater than 46%) and the estimated glucose is also high, then according to Table 1, the test time $T_{SS}$ for the system to measure the signal output of test chamber would be about 3.6 seconds. On the other hand, if the measured hematocrit is low (e.g., less than 38%) and the estimated glucose is low then according to Table 1, the specified sampling test time $T_{SS}$ for the system to measure the signal output of test chamber would be about 5.5 seconds.

Once the signal output $I_T$ of the test chamber is measured at the designated time (which is governed by the measured or estimated physical characteristic), the signal $I_T$ is thereafter used in the calculation of the analyte concentration (in this case glucose) with Equation 5 below.

$$G_0 = \left[\frac{I_T - \text{Intercept}}{\text{Slope}}\right] \qquad \text{Eq. 5}$$

where $G_0$ represents an analyte concentration;

$I_T$ represents a signal (proportional to analyte concentration) determined from the sum of the end signals measured at a specified sampling time $T_{SS}$, which may be the total current measured at the specified sampling time $T_{SS}$;

Slope represents the value obtained from calibration testing of a batch of test strips of which this particular strip comes from and is typically about 0.02; and Intercept represents the value obtained from calibration testing of a batch of test strips of which this particular strip comes from and is typically from about 0.6 to about 0.7.

It should be noted that the step of applying the first signal and the driving of the second signal is sequential in that the order may be the first signal then the second signal or both signals overlapping in sequence; alternatively, the second signal first then the first signal or both signals overlapping in sequence. Alternatively, the applying of the first signal and the driving of the second signal may take place simultaneously.

In the method, the step of applying of the first signal involves directing an alternating signal provided by an appropriate power source (e.g., the meter 200) to the sample so that a physical characteristic of the sample is determined from an output of the alternating signal. The physical characteristic being detected may be one or more of viscosity, hematocrit or density. The directing step may include driving first and second alternating signal at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" or "oscillating signal" can have some portions of the signal alternating in polarity or all alternating current signal or an alternating current with a direct current offset or even a multi-directional signal combined with a direct-current signal.

Further refinements of Table 1 based on additional investigations of the technique allowed applicants to devise Table 2, shown below.

TABLE 2

Specified Sampling Time $T_{SS}$ to Estimated G and Measured or Estimated Physical Characteristic

| Estimated G [mg/dL] | Measured or Estimated Physical Characteristic (e.g., HCT [%]) | | | | | | | | | | | | |
|---|---|---|---|---|---|---|---|---|---|---|---|---|---|
| | 24 | 27 | 30 | 33 | 36 | 39 | 42 | 45 | 48 | 51 | 54 | 57 | 60 |
| 25  | 4.6 | 4.6 | 4.5 | 4.4 | 4.4 | 4.4 | 4.3 | 4.3 | 4.3 | 4.2 | 4.1 | 4.1 | 4.1 |
| 50  | 5   | 4.9 | 4.8 | 4.7 | 4.7 | 4.6 | 4.5 | 4.4 | 4.3 | 4.2 | 4.1 | 4   | 4   |
| 75  | 5.3 | 5.3 | 5.2 | 5   | 4.9 | 4.8 | 4.7 | 4.5 | 4.4 | 4.3 | 4.1 | 4   | 3.8 |
| 100 | 5.8 | 5.6 | 5.4 | 5.3 | 5.1 | 5   | 4.8 | 4.6 | 4.4 | 4.3 | 4.1 | 3.9 | 3.7 |
| 125 | 6.1 | 5.9 | 5.7 | 5.5 | 5.3 | 5.1 | 4.9 | 4.7 | 4.5 | 4.3 | 4.1 | 3.8 | 3.6 |
| 150 | 6.4 | 6.2 | 5.9 | 5.7 | 5.5 | 5.3 | 5   | 4.8 | 4.6 | 4.3 | 4   | 3.8 | 3.5 |
| 175 | 6.6 | 6.4 | 6.2 | 5.9 | 5.6 | 5.4 | 5.2 | 4.9 | 4.6 | 4.3 | 4   | 3.7 | 3.4 |
| 200 | 6.8 | 6.6 | 6.4 | 6.1 | 5.8 | 5.5 | 5.2 | 4.9 | 4.6 | 4.3 | 4   | 3.7 | 3.4 |
| 225 | 7.1 | 6.8 | 6.5 | 6.2 | 5.9 | 5.6 | 5.3 | 5   | 4.7 | 4.3 | 4   | 3.6 | 3.2 |
| 250 | 7.3 | 7   | 6.7 | 6.4 | 6   | 5.7 | 5.3 | 5   | 4.7 | 4.3 | 4   | 3.6 | 3.2 |
| 275 | 7.4 | 7.1 | 6.8 | 6.4 | 6.1 | 5.8 | 5.4 | 5   | 4.7 | 4.3 | 4   | 3.5 | 3.2 |
| 300 | 7.5 | 7.1 | 6.8 | 6.5 | 6.2 | 5.8 | 5.5 | 5.1 | 4.7 | 4.3 | 4   | 3.5 | 3.1 |
| w325| 7.6 | 7.3 | 6.9 | 6.5 | 6.2 | 5.8 | 5.5 | 5.1 | 4.7 | 4.3 | 3.9 | 3.5 | 3.1 |
| 350 | 7.6 | 7.3 | 7   | 6.6 | 6.2 | 5.8 | 5.5 | 5.1 | 4.7 | 4.3 | 3.9 | 3.5 | 3.1 |
| 375 | 7.7 | 7.3 | 7   | 6.6 | 6.2 | 5.8 | 5.5 | 5.1 | 4.7 | 4.3 | 3.9 | 3.5 | 3.1 |
| 400 | 7.7 | 7.3 | 6.9 | 6.5 | 6.2 | 5.8 | 5.4 | 5   | 4.7 | 4.3 | 3.9 | 3.5 | 3.1 |
| 425 | 7.3 | 7.3 | 6.9 | 6.5 | 6.2 | 5.8 | 5.4 | 5   | 4.6 | 4.3 | 3.8 | 3.5 | 3.1 |
| 450 | 7.6 | 7.2 | 6.8 | 6.4 | 6.1 | 5.7 | 5.3 | 5   | 4.6 | 4.3 | 3.8 | 3.5 | 3.1 |
| 475 | 7.4 | 7.1 | 6.7 | 6.4 | 6   | 5.6 | 5.3 | 4.9 | 4.6 | 4.2 | 3.8 | 3.5 | 3.1 |
| 500 | 7.3 | 7   | 6.6 | 6.2 | 5.9 | 5.5 | 5.2 | 4.9 | 4.5 | 4.1 | 3.8 | 3.5 | 3.2 |
| 525 | 7.1 | 6.8 | 6.5 | 6.1 | 5.8 | 5.5 | 5.1 | 4.8 | 4.4 | 4.1 | 3.8 | 3.5 | 3.2 |
| 550 | 7   | 6.7 | 6.3 | 5.9 | 5.6 | 5.3 | 5   | 4.7 | 4.4 | 4.1 | 3.8 | 3.5 | 3.2 |
| 575 | 6.8 | 6.4 | 6.1 | 5.8 | 5.5 | 5.2 | 4.9 | 4.6 | 4.3 | 4.1 | 3.8 | 3.5 | 3.4 |
| 600 | 6.5 | 6.2 | 5.9 | 5.6 | 5.3 | 5   | 4.7 | 4.5 | 4.3 | 4   | 3.8 | 3.6 | 3.4 |

As in Table 1, a measured or estimated physical characteristic is used in Table 2 along with an estimated analyte concentration to derive a time $T_{SS}$ at which the sample is to be measured. For example, if the measured characteristic is about 30% and the estimated glucose (e.g., by sampling at Tes of about 2.5 to 3 seconds) is about 350, the time at which the microcontroller should sample the fluid is about 7 seconds. In another example, where the estimated glucose (measured at Tes) is about 300 mg/dL and the measured or estimated physical characteristic is 60%, the specified sampling time $T_{SS}$ would be about 3.1 seconds.

For the embodiments utilized with Table 2, the estimated glucose concentration is provided with an equation:

$$G_{est} = \frac{(I_E - x_2)}{x_1} \quad \text{Eq. 6}$$

where $G_{est}$ represents the estimated glucose concentration;
$I_E$ is the signal measured at about 2.5 seconds;
$x_1$ is the slope (e.g., $x_1$=1.3e01);
$x_2$ is the intercept (e.g., $x_2$=6.9e02)

From the estimated glucose, the glucose concentration can be determined from:

$$G_O = \frac{(I_S - x_4)}{x_3} \quad \text{Eq. 7}$$

where:

$G_O$ represents the glucose concentration;
$I_S$ is the signal measured at a specified sampling time $T_{SS}$ from Table 2;
$x_3$ is the slope (e.g., $x_3$=9.6); and
$x_4$ is the intercept (e.g., $x_4$=4.8e02).

Although applicant's technique may specify only one sampling time point, the method may include sampling as many time points as required, such as, for example, sampling the signal output continuously (e.g., at specified sampling time such as, every 1 milliseconds to 100 milliseconds) from the start of the test sequence until at least about 10 seconds after the start and the sampling results stored for processing near the end of the test sequence. In this variation, the sampled signal output at the specified sampling time (which may be different from the predetermined sampling time point) is the value used to calculate the analyte concentration.

It is noted that in the preferred embodiments, the measurement of a signal output for the value that is somewhat proportional to analyte (e.g., glucose) concentration is performed prior to the estimation of the hematocrit. Alternatively, the hematocrit level can be estimated prior to the measurement of the preliminary glucose concentration. In either case, the estimated glucose measurement $G_E$ is obtained by Equation 3.3 with $I_E$ sampled at about one of 2.5 seconds or 5 seconds, as in FIG. 7, the physical characteristic (e.g., Hct) is obtained by Equation 4 and the glucose measurement G is obtained by using the measured signal output $I_D$ at the designated sampling time point(s) (e.g., the measured signal output $I_D$ being sampled at 3.5 seconds or 6.5 seconds) for the signal transient 1000.

Other techniques for determining the analyte concentration or value are shown and described in PCT/GB2012/053276 filed on Dec. 28, 2012, PCT/GB2012/053279 filed on Dec. 28, 2012; PCT/GB2012/053277 filed on Dec. 28, 2012, all of the applications are hereby incorporated by reference as if fully set forth herein with a copy attached to the appendix of this application.

It has been determined by applicants that any problem of the conductive surface on one of the working electrodes (e.g., fouling) will reduce the output signal transient linked to that electrode. This will manifest as a low current transient with a low bias. In general these anomalous results are detected by our system error check (shown and describe in U.S. patent application Ser. No. 13/929,404 Filed on 27 Jun. 2013, entitled as: FILL ERROR TRAP FOR AN ANALYTE MEASUREMENT DETERMINED FROM A SPECIFIED SAMPLING TIME DERIVED FROM A SENSED PHYSICAL CHARACTERISTIC OF THE SAMPLE CONTAINING THE ANALYTE, which is incorporated by reference herein this application). This system error check looks for large differences between the first working electrode and second working electrode signal transients.

We have determined that if fouling occurs on the counter or reference electrode, the system will generate low signal output transients on both first working electrode 12 and second working electrode 14 as the system will be limited by the reduced efficiency of the counter or reference electrode 10. Our prior system error check will not work here, as both first working electrode 12 and second working electrode 14 will be similarly impacted. A system error trap is therefore required that will limit this potential failure mode.

Consequently, we have devised a solution to this problem of determining when to annunciate that there is an error due to fouling or damaged reference electrode of the test strip. In particular, applicant has devised a test in which a first difference is determined from the magnitude of the output signal transient for the first electrode measured proximate the specified sampling time $T_{SS}$ to the output signal transient for the first working electrode measured proximate the predetermined sampling time $T_{Pdt}$.

Also in this test, a second difference is determined from the magnitude of the output signal transient for the second electrode measured proximate the specified sampling time $T_{SS}$ to the output signal transient for the second working electrode measured proximate the predetermined sampling time $T_{Pdt}$. If either of the first difference or second difference is less than bias threshold $\beta$ then an error is flagged or stored in the system.

The mathematical representation of the evaluation that would trigger an error is shown by Equations 8.1 and 8.2:

$$(I_{we1@PdT} - I_{we1@T_{SS}}) < \beta \qquad \text{Eq. 8.1}$$

$$(I_{we2@PdT} - I_{we2@T_{SS}}) < \beta \qquad \text{Eq. 8.2}$$

where
each of the output signals (for first working electrode 12) Iwe1 (in microamp) and (for second working electrode 14) Iwe2 (in microamp) are measured at the "specified sampling time" (or $T_{SS}$) and predetermined sampling $T_{Pdt}$ as discussed earlier and $\beta$ is any value from about 10 nano-amperes to 1000 nanoamperes and preferably about 100 nanoamperes.

Referring to FIG. 5, a novel implementation of our error check process is illustrated during an analyte test measurement or assay of a test analyte (e.g., blood or control solution). At step 604, a drop of test analyte is deposited on the biosensor (i.e., FIGS. 3A-3C) with the biosensor inserted previously inserted (step 602) into a meter (FIG. 1A or 1B). At step 604, the meter cycles through a fill detect sequence (FIG. 4A) and once the meter (via its microcontroller 300 in FIG. 2A or 2B) detects fluid, the meter moves to step 606 at which point a test sequence timer Ts is set to zero (FIG. 4A).

The meter begins a measurement of the physical characteristic of the analyte by driving a time varying signal (e.g., alternating or oscillating signal) into the analyte sample and measuring response output from the sample (via sensing electrodes 19a and 20a in FIG. 3A). The meter may also drive a direct signal (i.e., D.C. signal) into the analyte samples and take a measurement at a predetermine time (during the test sequence) to obtain an estimated analyte value. The meter also determines at step 612 a specific sampling time ("$T_{SS}$") based on the measured physical characteristic (e.g., impedance Z at step 608) and the estimated analyte concentration (from step 610) using either the look-up tables described herein or algorithms described in PCT/GB2012/053276; PCT/GB2012/053279; or PCT/GB2012/053277.

Once the meter has obtained the specified sampling time $T_{SS}$ from step 612, it will sample or measure the output signals from the analyte sample (via the working electrodes 1 and 2) at the designated time $T_{SS}$ during the test at step 614. The meter will also sample or measure at step 616 the output signals from the analyte sample (via the working electrodes 1 and 2) at a predetermined time slot. In this embodiment, we have selected the predetermined time slot to be the same as the time slot used for estimating the analyte measurement at approximately 2.5 seconds (e.g., $T_{Pdt}$=Tes) into the test sequence.

At step 618, the meter will calculate a first differential Δ1 in the response of the first working electrode 12 at these two time slots (i.e., the specified time $T_{SS}$ and the predetermined time $T_{Pdt}$). At step 620, the meter will calculate a second differential Δ2 in the response of the second working electrode 14 at these two time slots (i.e., the specified time $T_{SS}$ and the predetermined time $T_{Pdt}$).

From step 620, the meter can proceed directly to step 628 whereby each of the differentials Δ1 or Δ2 can be checked against a threshold β. Threshold β can be designated as a function of the measured physical characteristic (e.g., hematocrit). It should be noted that the bias threshold β can be any value from about 30 nanoamperes to 1000 nanoamperes. Based on our initial experimentations, we have selected 100 nanoamperes for this threshold. If any of the differentials Δ1 or Δ2 is less than bias threshold β then an error flag can be set at step 630 for display at the end of the test sequence being conducted via the main routine (or the test measurement sequence can be immediately terminated with a display of the error). It is noted that where the Δ1 or Δ2 is a negative value, the system can obtain an absolute value for comparison to the predetermined threshold.

Given the similarity of the output signal transients of this error to output signal transients at low temperatures for certain embodiments of the test strip, we can devise this error check to be disabled below a certain temperature threshold (e.g., $T_{threshold}$~16 deg. Celsius) to avoid large numbers of good measurements taken at low temperature being eliminated. We have also configured the test so that it can be limited to instances where the estimated analyte is less than a given threshold (e.g., glucose concentration Gmax being less than 275 mg/dL). To better control false positives, we can also set another condition precedent in which the test is carried out only if the measured physical characteristic (e.g., hematocrit or Z) is less than a maximum value (e.g., Zmax).

Depending on the parameters of the test strips and the meter, these threshold conditions can be established as condition precedent steps 622, 624, and 626 into the method illustrated in FIG. 5. Although these condition precedents have been established for our particular configuration of the test strip and measurement system, it should be understood that these conditions are not required as part of this reference electrode error check.

While the invention has been described in terms of particular variations and illustrative Figures, those of ordinary skill in the art will recognize that the invention is not limited to the variations or Figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

The invention claimed is:

1. An analyte measurement system with electrode error determination, the system comprising:
 a test strip including:
  a substrate;
  a plurality of electrodes connected to respective electrode connectors with a reagent disposed proximate the plurality of the electrodes, the plurality of electrodes comprising:
   physical characteristic sensing electrodes;
   a first working electrode and a second working electrode; and
   a reference electrode; and
 an analyte meter including:
  a housing;
  a test strip port connector configured to connect to the respective electrode connectors of the test strip; and
  a microprocessor in electrical communication with the test strip port connector to apply electrical signals or measure electrical signals from the plurality of electrodes, wherein the microprocessor is configured to:
   (a) apply a first signal to the physical characteristic sensing electrodes of the plurality of electrodes to determine a physical characteristic of a fluid sample;
   (b) apply a second signal between the first working electrode and the reference electrode, and between the second working electrode and the reference electrode to determine an analyte concentration of the fluid sample;
   (c) measure a signal output proximate a specified sampling time point from each of the first and second working electrodes;
   (d) measure another signal output proximate a predetermined sampling time point from each of the first and second working electrodes;
   (e) calculate a first differential between a signal output of the first working electrode measured at the specified sampling time point and a signal output of the first working electrode measured at the predetermined sampling time point;
   (f) calculate a second differential between a signal output of the second working electrode measured at the specified sampling time point and a signal output of the second working electrode measured at the predetermined sampling time point;
   (g) evaluate whether any one of the first differential and second differential is less than a predetermined threshold to determine an error; and
   (h) in the event one of the first and second differentials is less than a bias threshold then annunciate the error.

2. The system of claim 1, in which the plurality of electrodes are commonly disposed in a chamber provided on the substrate.

3. The system of claim 2, in which the plurality of electrodes is disposed on the same plane defined by the substrate.

4. The system of claim 2, in which the reagent is disposed proximate the first and second working electrodes and no reagent is disposed on the physical characteristic sensing electrodes.

5. The system of claim 1, in which the error is annunciated when both the first and second differential thresholds are less than the predetermined threshold.

6. The system of claim 1, in which the predetermined threshold comprises about 100 nanoamperes.

\* \* \* \* \*